United States Patent
Huff et al.

(10) Patent No.: US 6,389,874 B1
(45) Date of Patent: May 21, 2002

(54) FUEL COMPOSITION SENSOR RATIONALITY TEST

(75) Inventors: Shean P. Huff, Ann Arbor; Jerry Kennie, Canton; Richard K. Moote, Ann Arbor; John M. Prevost, Jackson, all of MI (US)

(73) Assignee: DaimlerChrysler Corporation, Auburn Hills, MI (US)

( * ) Notice: Subject to any disclaimer, the term of this patent is extended or adjusted under 35 U.S.C. 154(b) by 0 days.

(21) Appl. No.: 09/397,750

(22) Filed: Sep. 16, 1999

(51) Int. Cl.$^7$ ............................................... G01D 18/00
(52) U.S. Cl. ....................................................... 73/1.02
(58) Field of Search .............................. 73/1.02, 118.1; 701/34

(56) References Cited

U.S. PATENT DOCUMENTS

| | | | | |
|---|---|---|---|---|
| 5,150,683 A | * | 9/1992 | Depa et al. | |
| 5,205,151 A | * | 4/1993 | Shimamura et al. | ......... 73/1.02 |
| 5,400,762 A | * | 3/1995 | Fodale et al. | |
| 5,550,478 A | * | 8/1996 | Kopera | |
| 5,850,824 A | * | 12/1998 | Seitz et al. | |
| 5,868,117 A | * | 2/1999 | Moote et al. | |
| 5,881,703 A | * | 3/1999 | Nankee, II et al. | |
| 5,901,671 A | * | 5/1999 | Huff et al. | |
| 5,915,342 A | * | 6/1999 | Huff et al. | |
| 5,937,798 A | * | 8/1999 | Cheng et al. | |
| 5,941,217 A | * | 8/1999 | Cheng et al. | |

* cited by examiner

Primary Examiner—Robert Raevis
(74) Attorney, Agent, or Firm—Mark P. Calcaterra

(57) ABSTRACT

A method is provided for monitoring the integrity of a fuel composition sensor in a flexible fueled vehicle. At ignition-on, the fuel composition sensor is tested for electrical and rationality viability. After ignition-on, the fuel composition is periodically, non-intrusively, tested for potential rationality errors. Should the non-intrusive testing indicate that a potential error exists, the fuel composition sensor is intrusively tested for rationality errors. If the intrusive test detects that the fuel composition sensor is malfunctioning, the engine control system converts to a limp-in mode and sets the engine operating parameters based on feedback from an exhaust gas oxygen sensor system.

13 Claims, 5 Drawing Sheets

FUEL COMPOSITION SENSOR RATIONALITY TEST

BACKGROUND OF THE INVENTION

1. Technical Field

The present invention generally relates to flexible fueled vehicles and, more particularly, to a method for determining the integrity of a fuel composition sensor in the flexible fueled vehicle.

2. Discussion

A flexible fueled vehicle is a vehicle which is capable of operating on different fuels such as gasoline, alcohol, or any mixture of the two. Modifications to the operating parameters of an engine are necessary when operating on different fuels due to the different combustion characteristics of each fuel. For example, an engine operating on a fuel including a high percentage of alcohol requires a greater ratio of fuel-to-air as compared to an engine operating on a fuel including a high percentage of gasoline. If the fuel-to-air ratio is set incorrectly (i.e., non-stoichiometric), perfect combustion cannot be achieved. This may lead to rough engine operation and/or poor emissions.

Flexible fueled vehicles are often equipped with a fuel composition sensor for determining the nature of the particular fuel mixture delivered to the engine. The fuel composition sensor is disposed along a fuel line and senses select characteristic of the fuel which indicates the concentration of alcohol (i.e., optical, conductivity, capacitive, etc.) of the fluid passing thereby. In response, the fuel composition sensor generates a voltage signal indicative of the particular fuel mixture being delivered to the engine. The voltage signal is sent to the engine control system which sets the fuel-to-air ratio for the engine in accordance therewith.

Unfortunately, modern flexible fueled vehicles do not incorporate a mechanism for detecting a malfunctioning fuel composition sensor. As such, the engine control system may set an improper fuel-to-air ratio for the engine based on the voltage signal from the malfunctioning fuel composition sensor. This could cause rough engine operation, poor emissions, and/or engine damage.

In view of the foregoing, there is a need in the art for a control system for monitoring the functioning of a fuel composition sensor such that malfunctions may be detected.

SUMMARY OF THE INVENTION

The above and other objects are provided by a method for determining the integrity of a fuel composition sensor. The method includes testing the fuel composition sensor at an ignition on event for electrical and rational integrity. The electrical check determines whether the fuel composition sensor voltage is shorted high or shorted low, and also tests for electrical continuity. The rational check determines whether the voltage signal from the fuel composition sensor at the ignition-on event is within a calibratible threshold of the last voltage signal received from the fuel composition sensor before the previous ignition-off event. If the fuel composition sensor fails either the ignition-on electrical or rational checks, a fault code is set and the engine control system converts to a fuel composition sensor limp-in mode.

If the fuel composition sensor passes the ignition-on electrical and rational checks, the engine control system operates in a normal mode employing the output signal from the fuel composition sensor as a basis for setting the fuel-to-air ratio for the engine. During normal operation, the fuel composition sensor is periodically tested for potential rationality malfunctions. These periodic rationality tests are non-intrusive in nature and do not set a fault code by themselves but only enable a second, intrusive-type, check. The non-intrusive testing includes three different determinations.

The first non-intrusive check is triggered when the fuel level increases greater than a fuel volume added threshold. Upon this occurrence, the fuel composition sensor output value is compared to two projected fuel composition possibilities. This check assumes that either a low or high concentration of alcohol based fuel was added to the fuel tank. If the fuel composition sensor output value differs by more than a calibratible amount from the two projected fuel composition possibilities, a flag is set for the engine control system to conduct additional, intrusive-type, testing.

The second non-intrusive check of the fuel composition sensor continuously monitors the system for an unexpected shift in the amount of fuel delivered to the engine. If the amount of fuel delivered varies more than a calibratible amount, as compared to nominal operating conditions, a flag is set for the engine control system to conduct additional, intrusive-type, testing.

The third non-intrusive check of the fuel composition sensor involves continuously monitoring the fuel composition sensor's output for a significant deviation from a previously stored, fully updated, fuel composition sensor output value in the absence of a fuel fill trigger. If the current fuel composition sensor output value is more than a calibratible difference from the stored, fully updated fuel composition sensor value, a flag is set for the engine control system to conduct additional, intrusive-type, testing.

Upon the failure of any of the three non-intrusive checks, intrusive testing is conducted. The intrusive testing involves learning the composition of the fuel by way of the vehicle's exhaust gas oxygen sensor feedback system. The fuel composition determined by the exhaust gas oxygen sensor feedback system is compared to the fuel composition sensor output value. If the difference between the two values is greater than a predetermined threshold, the engine control system converts to a limp-in mode. In the limp-in mode, the exhaust gas oxygen sensor feedback system is used to determine the composition of the fuel and the fuel-to-air ratio for the engine is set in accordance therewith.

BRIEF DESCRIPTION OF THE DRAWINGS

In order to appreciate the manner in which the advantages and objects of the invention are obtained, a more particular description of the invention will be rendered by reference to specific embodiments thereof which are illustrated in the appended drawings. Understanding that these drawings only depict preferred embodiments of the present invention and are not therefore to be considered limiting in scope, the invention will be described and explained with additional specificity and detail through the use of the accompanying drawings in which.

DETAILED DESCRIPTION OF THE PREFERRED EMBODIMENT

The present invention is directed towards a method of monitoring the integrity of a fuel composition sensor in a flexible fueled vehicle. At ignition-on, the fuel composition sensor is tested for electrical and rationality viability. After ignition-on, the fuel composition is periodically, non-intrusively, tested for potential rationality errors. Should the non-intrusive testing indicate that a potential error exists, the fuel composition sensor is intrusively tested for rationality errors. If the intrusive test detects that the fuel composition sensor is malfunctioning, the engine control system converts to a limp-in mode and sets the engine operating parameters based on feedback from an exhaust gas oxygen sensor system.

Figure 1:
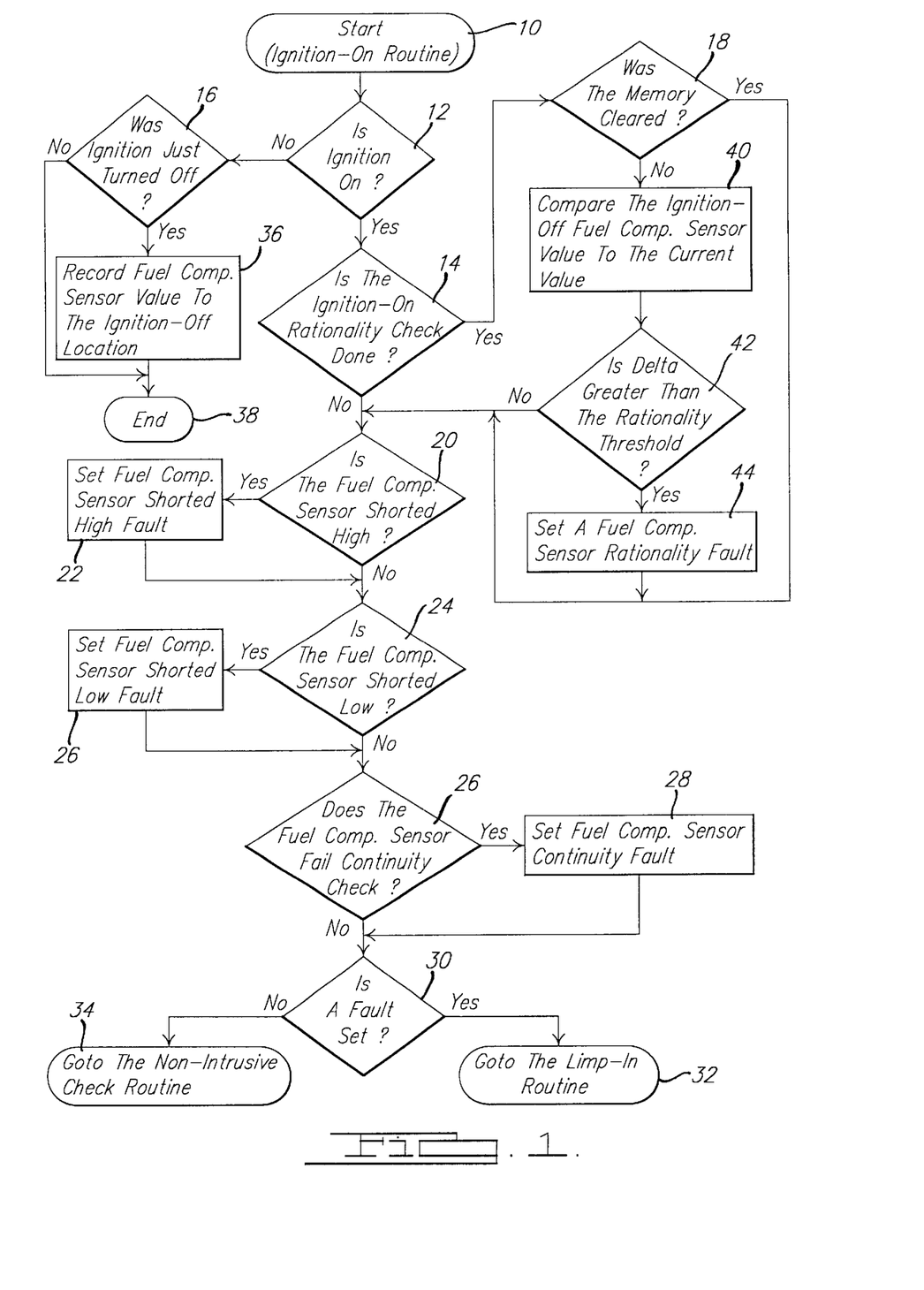
FIG. 1 is a flowchart depicting a methodology for conducting ignition-on electrical and rationality testing of the fuel composition sensor according to the present invention.

Turning now to the drawing figures, FIG. 1 illustrates the methodology for determining the integrity of the fuel composition sensor at an ignition-on event. The methodology starts in bubble 10 and falls through to decision block 12. In decision block 12, the methodology determines whether the vehicle ignition is on. If so, the methodology continues to decision block 14. However, if the ignition is not on at decision block 12, the methodology advances to decision block 16.

In decision block 14, the methodology determines whether the ignition-on rationality check has been done. If so, the methodology advances to decision block 18. If the ignition-on rationality check has not been done at decision block 14, the methodology advances to decision block 20.

In decision block 20, the methodology tests the fuel composition sensor to determine if the sensor voltage is shorted high If the fuel composition sensor is shorted high at decision block 20, the methodology advances to block 22. In block 22, the methodology sets a fault code indicating that the fuel composition sensor is shorted high. After setting the fuel composition sensor shorted high fault code at block 22, or if the fuel composition sensor output voltage is not shorted high at decision block 20, the methodology advances to decision block 24.

In decision block 24, the methodology tests the fuel composition sensor to determine if the sensor is shorted low. If the fuel composition sensor is shorted low at decision block 24, the methodology advances to block 26. In block 26, the methodology sets a fault code indicating that the fuel composition sensor voltage is shorted low. After setting the fuel composition sensor shorted low fault code at block 26, or if the fuel composition sensor is not shorted low at decision block 24, the methodology advances to decision block 26.

In decision block 26, the methodology tests the fuel composition sensor for its electrical continuity. If the fuel composition sensor fails the continuity check at decision block 26, the methodology advances to block 28. In block 28, the methodology sets a fault code indicating that the fuel composition sensor electrical continuity is malfunctioning. After setting the fuel composition sensor continuity fault code at block 28, or if the fuel composition sensor passes the continuity check at decision block 26, the methodology advances to decision block 30.

In decision block 30, the methodology determines whether a fault code has been set. If so, the methodology advances to bubble 32. In bubble 32, the methodology implements a limp-in routine to convert the engine control system from reliance on the output from the fuel composition sensor to reliance on feedback from the exhaust gas oxygen sensor system. However, if no fault code is set at decision block 30, the methodology advances to bubble 34. In bubble 34, the methodology implements a non-intrusive check routine to periodically monitor the fuel composition sensor for potential errors.

Referring again to decision block 12, if the methodology determines that the ignition is not on at decision block 12, the methodology advances to decision block 16. In decision block 16, the methodology determines if the ignition was just turned off. If so, the methodology advances to block 36. In block 36, the methodology records the output voltage value of the fuel composition sensor to an ignition-off location of the engine controller memory. After recording the fuel composition sensor value to the ignition-off location in block 36, or if the ignition is determined to not have been just turned off at decision block 16, the methodology advances to bubble 38. In bubble 38, the methodology exits the subroutine pending a subsequent execution thereof such as, for instance, at the next ignition-on event.

Referring again to decision block 14, if the ignition-on rationality check has been done at decision block 14, the methodology advances to decision block 18. In decision block 18, the methodology determines whether the engine controller memory has been cleared. This would occur, for instance, if the vehicle battery is disconnected. If the engine controller memory has been cleared at decision block 18, the methodology advances to decision block 20 to check the fuel composition sensor voltage for a shorted high condition as described above. However, if the methodology determines that the engine controller memory was not cleared at decision block 18, the methodology continues to block 40.

In block 40, the methodology compares the value of the ignition-off fuel composition sensor output recorded at block 36 to the current fuel composition sensor output value. From block 40, the methodology continues to decision block 42. In decision block 42, the methodology determines whether the difference between the ignition-off fuel composition sensor value and the current fuel composition sensor value is greater than a preselected rationality threshold. Preferably, the predetermined rationality threshold is approximately equal to a value which corresponds to a 10% fuel-to-air ratio error.

If the difference between the ignition-off fuel composition sensor value and the current fuel composition sensor value is greater than the rationality threshold at decision block 42, the methodology continues to block 44. In block 44, the methodology sets a fault code indicating that the fuel composition sensor rationality is malfunctioning. After setting the fuel composition sensor rationality fault code at block 44, or if the difference between the ignition off fuel composition sensor value and the current fuel composition sensor value is not greater than the rationality threshold at decision block 42, the methodology advances to decision block 20 which was previously described.

Figure 2A:
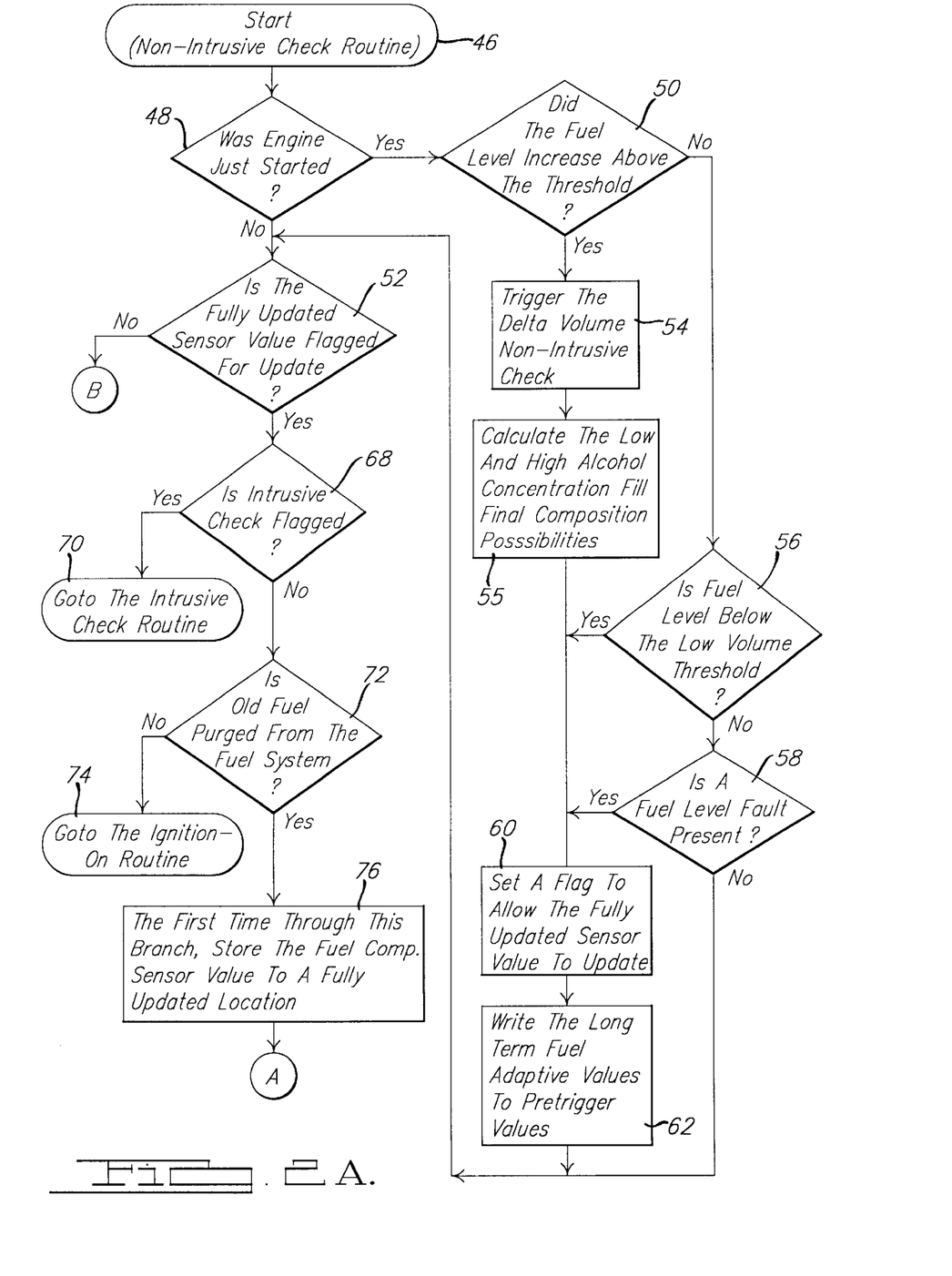
FIG. 2A is a flowchart depicting a methodology for conducting periodic, non-intrusive, rationality testing of the fuel composition sensor according to the present invention.

Referring again to decision block 30, if the methodology determines that no fault code has been set at decision block 30, the methodology advances to bubble 34 where it implements a non-intrusive check routine. Turning now to FIG. 2A, the non-intrusive check routine is illustrated. The non-intrusive check routine starts in bubble 46 and falls through to decision block 48.

In decision block 48, the methodology determines whether the engine was just started. If so, the methodology advances to decision block 50. However, if the methodology determines that the engine has not just been started at decision block 48, the methodology advances to decision block 52.

In decision block 50, the methodology determines whether the fuel level has increased greater than a fuel volume added threshold. If so, a fuel fill event is assumed to have occurred and the methodology advances to block 54. In block 54, the methodology sets a flag to trigger a delta volume non-intrusive check of the fuel composition sensor which is described in greater detail below. However, if the methodology determines that the fuel level has not increased above the threshold value at decision block 50, the methodology advances to decision block 56.

In decision block 56, the methodology determines whether the fuel level is below a low volume threshold value. If the fuel level is not below the low volume threshold at decision block 56, the methodology continues to decision block 58. In decision block 58, the methodology determines whether a fuel level sensor fault code is set. If the methodology determines that no fuel level sensor fault code is present at decision block 58, the methodology advances to decision block 52.

After triggering the delta volume non-intrusive check at block 54, the methodology continues to block 55. In block 64, the methodology calculates two fuel composition possibilities based on the assumption that either a low alcohol concentration fuel or a high alcohol concentration fuel was added to the fuel tank. The two fuel composition possibilities are calculated based on the fuel composition before the fuel fill event, the fuel volume before the fuel fill event, the total fuel volume after the fuel fill event, and the two likely fuel concentrations added to the fuel tank (e.g., 85% alcohol and 10% alcohol). After calculating the two fuel composition possibilities at block 55, or if the methodology determines that the fuel level is below the low volume threshold at decision block 56, or if the methodology determines that a fuel level sensor fault code is present at decision block 58, the methodology advances to block 60. In block 60, the methodology sets a flag to allow the fully updated fuel composition value to update. Since the only time the fuel composition can change is when fuel has been added to the tank, this is the only time that the fully updated fuel composition sensor value requires revision. Certain triggers are used to determine when fuel is to have been added. The first trigger is if a fuel level sensor senses a fuel level increase which is greater than a fuel volume added threshold. This is accomplished at decision block 50. The second trigger is if the fuel level sensor senses that the fuel level has dropped below a low fuel volume threshold at an ignition-on event. When the fuel level is this low, fuel composition changes due to small volume additions or fuel level increases cannot be reliably detected. As such, updating of the fuel composition sensor value is thereafter triggered at each ignition-on event. This is accomplished at decision block 56. The final trigger is if the fuel level sensor is malfunctioning. Since the fuel level sensor is malfunctioning, it cannot be relied upon to detect fuel level changes. Therefore, the fuel composition sensor value update is thereafter triggered at each ignition-on event. This is accomplished at decision block 58.

From block 60, the methodology continues to block 62. In block 62, the long-term fuel adaptive values are written to the engine controller memory at a pretrigger location. The long-term fuel adaptive values are used should intrusive testing of the fuel composition sensor be required. Such intrusive testing is described below. From block 62, the methodology continues to decision block 52.

In decision block 52, the methodology determines whether the fully updated fuel composition sensor value has been flagged for an update. Such a flag would have been set at block 60 described above. If the fully updated fuel composition sensor value is determined to not have been flagged for an update at decision block 52, the methodology advances through connector B to decision block 66 illustrated in FIG. 2B. However, if the methodology determines that the fully updated fuel composition sensor value has been flagged for an update at decision block 52, the methodology advances to decision block 68.

In decision block 68, the methodology determines if a flag has been set indicating that an intrusive check of the fuel composition sensor should be performed. If the methodology determines that the intrusive check flag has been set at decision block 68, the methodology advances to bubble 70. In bubble 70, the methodology implements the intrusive check routine for determining if the rationality of the fuel composition sensor is malfunctioning. However, if the methodology determines that the intrusive check flag has not been set at decision block 68, the methodology advances to decision block 72.

In decision block 72, the methodology determines if the fuel within the system that has not mixed with the new fuel from the last fuel fill event has been ingested by the engine such that the fuel now being delivered to the engine is fully mixed. If the methodology determines that the old fuel is not yet purged from the fuel system at decision block 72, the methodology advances to bubble 74. In bubble 74, the methodology implements the ignition-on routine as described previously with reference to FIG. 1. However, if the methodology determines that the old fuel has been purged from the fuel system at decision block 72, the methodology advances to block 76. In block 76, the methodology stores the fuel composition sensor value to the engine controller memory at a fully updated location if, and only if, this is the first time the methodology is passing through block 76 after the most recent delta volume, low volume, or fuel level fault trigger. From block 76, the methodology advances through connector A to decision block 78 in FIG. 2B.

Figure 2B:
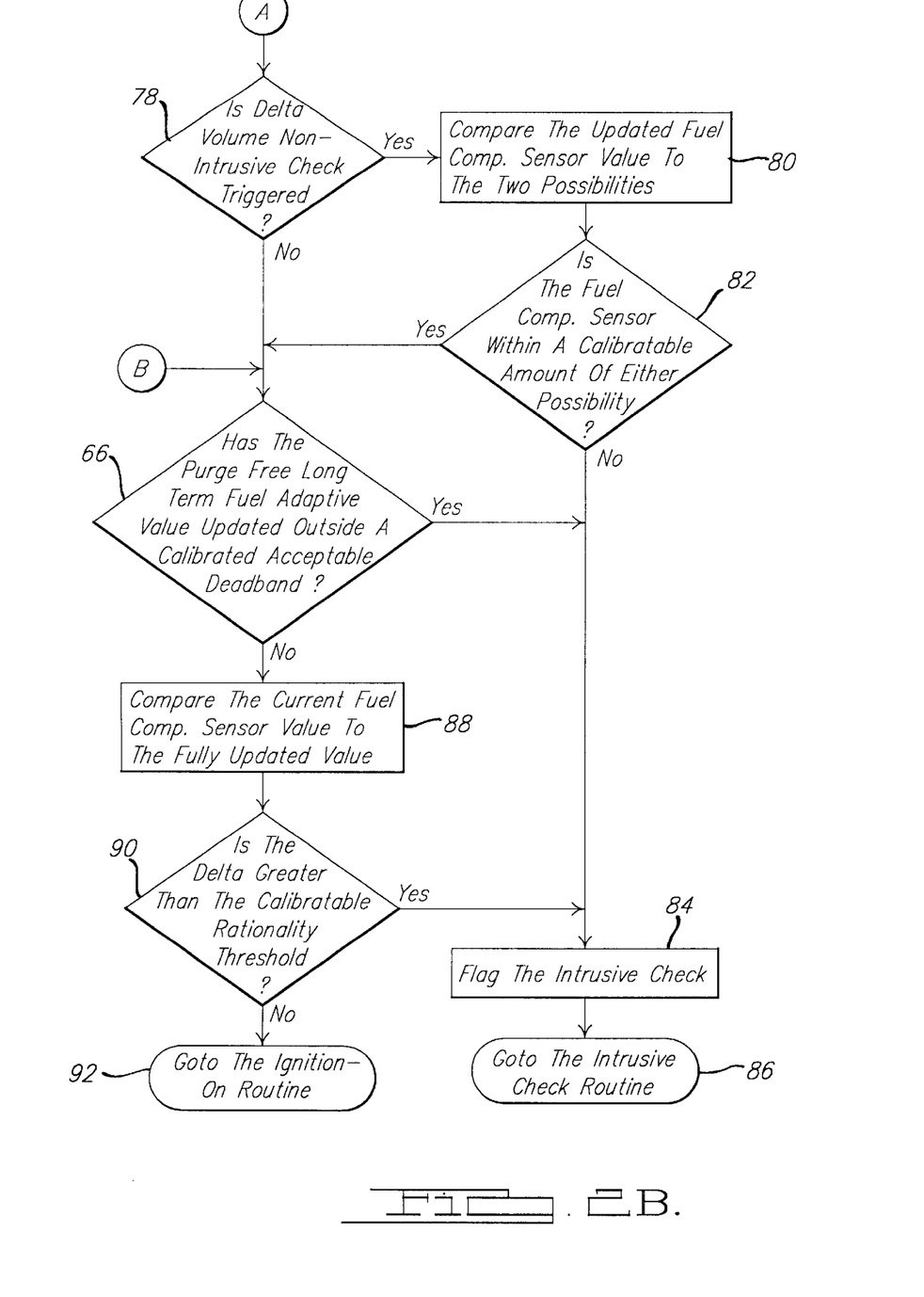
FIG. 2B is a flowchart depicting a continuation of the methodology of FIG. 2A.

Turning now to FIG. 2B, in decision block 78, the methodology determines whether the delta volume non-intrusive check has been triggered. This would have occurred at block 54 of FIG. 2A as described above. If the methodology determines that the delta volume non-intrusive check has not been triggered at decision block 78, the methodology advances to decision block 66. However, if the methodology determines that the delta volume non-intrusive check has been triggered at decision block 78, the methodology advances to block 80.

In block 80, the methodology compares the updated fuel composition sensor value to the two final fill composition possibilities determined at block 64. From block 80, the methodology continues to decision block 82. In decision block 82, the methodology determines if the fuel composition sensor output value is within a calibratible amount of the two final fill fuel composition possibilities. If so, the methodology advances to decision block 66. However, if the methodology determines that the fuel composition sensor is outside of the calibratible amount of either final fill fuel composition possibility in decision block 82, the methodology advances to block 84.

In block 84, the methodology sets a flag indicating that an intrusive check of the fuel composition sensor is required. From block 84, the methodology continues to bubble 86. In bubble 86, the methodology implements the intrusive check routine for verifying potential malfunctions of the rationality of the fuel composition sensor.

Referring again to decision block 66, the methodology determines whether the purge free long-term fuel adaptive value has updated outside of a calibrated acceptable deadband. This check determines if an unexpected shift in the fuel being delivered to the engine for maintaining a proper fuel-to-air mixture has occurred. That is, the long-term fuel adaptive values that are updated with the fuel vapor management system disabled are monitored (described below). If the long-term fuel adaptive values add or remove more than a calibratible amount of fuel, as compared to nominal operating conditions, a malfunction of the fuel composition sensor may be occurring. Therefore, if the methodology determines that the purge free long-term fuel adaptive value has been updated outside of a calibratible acceptable deadband at decision block 66, the methodology advances to block 84 and flags the engine control system for an intrusive check of the fuel composition sensor. However, if the methodology determines that the purge free long-term fuel adaptive value has been updated within the calibrated acceptable deadband at decision block 66, the methodology continues to block 88.

In block 88, the methodology compares the current fuel composition sensor value to the fully updated fuel composition sensor value. As described above, this check is triggered if the fuel level increases above an added fuel threshold at decision block 50, at each ignition-on event if the fuel level is below a low-volume threshold at decision block 56, or at each ignition-on event if a fuel level sensor fault is present at block 58. From block 88, the methodology continues to decision block 90.

In decision block 90, the methodology determines whether the difference between the current fuel composition sensor value and the fully updated fuel composition sensor value is greater than a calibratible rationality threshold value. If so, a potential malfunction of the fuel composition sensor is assumed to exist, and the methodology advances to block 84 to set a flag indicating that an intrusive check of the fuel composition sensor is required. However, if the difference between the current fuel composition sensor value and the fully updated fuel composition sensor value is not greater than the calibratible rationality threshold at decision block 90, the methodology advances to bubble 92. In bubble 92, the methodology implements the ignition-on routine which was described above with reference to FIG. 1.

Figure 3:
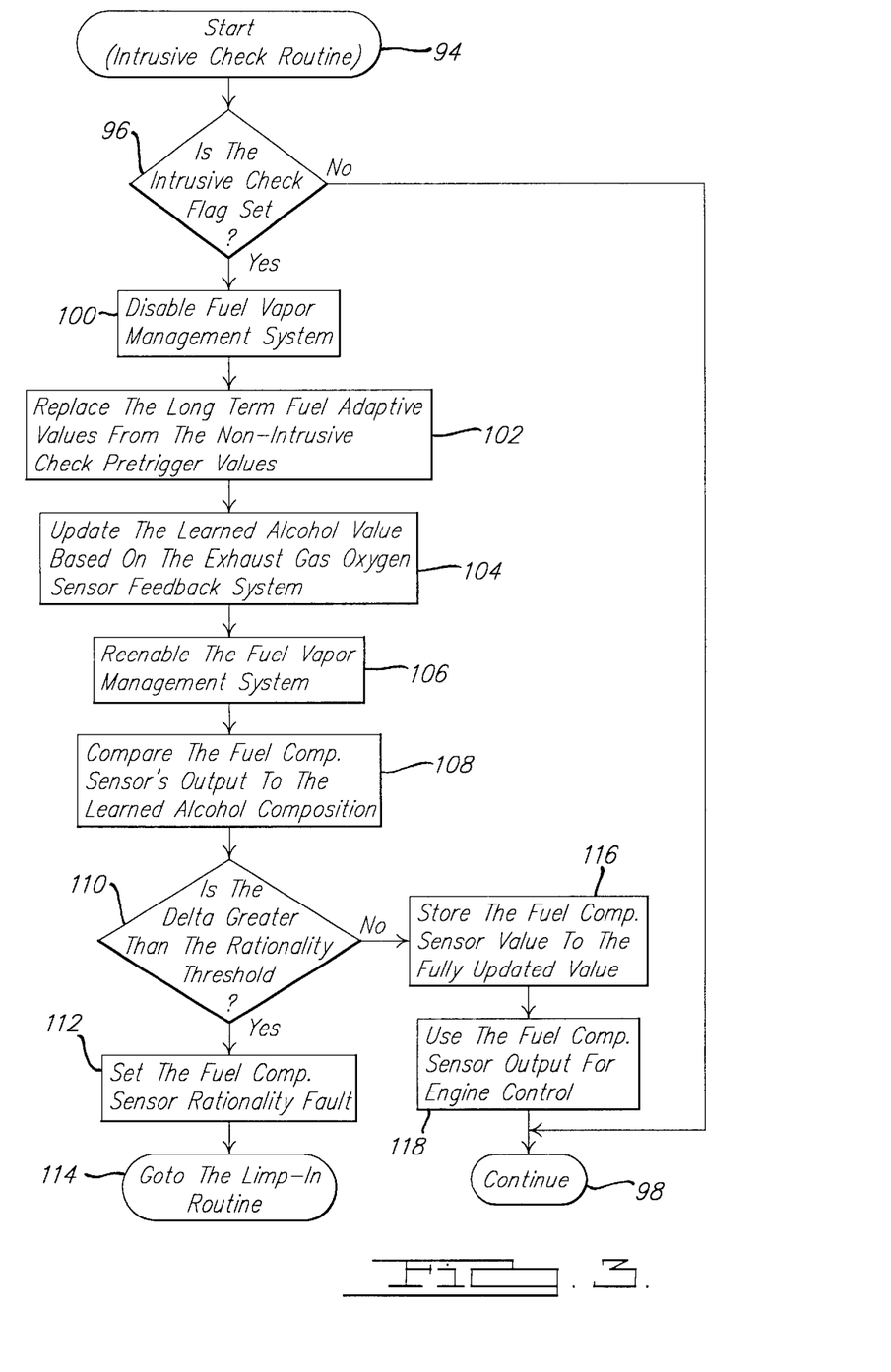
FIG. 3 is a flowchart depicting a methodology for conducting intrusive-type rationality testing of the fuel composition sensor according to the present invention.

Referring again to block 84, after the methodology has set the flag requiring an intrusive check of the fuel composition sensor at block 84, the methodology advances to bubble 86 where it implements the intrusive check routine. Turning now to FIG. 3, the intrusive check routine is illustrated. The intrusive check routine starts in bubble 94 and falls through to decision block 96.

In decision block 96, the methodology determines whether the intrusive check flag has been set. If not, the methodology advances to bubble 98 and exits the subroutine pending a subsequent execution thereof. However, if the methodology determines that the intrusive check flag has been set at decision block 96, the methodology continues to block 100.

In block 100, the methodology disables the flexible fueled vehicle's vapor management system. From block 100, the methodology continues to block 102. In block 102, the methodology replaces the long-term fuel adaptive values with the long-term fuel adaptive values recorded at block 52. From block 102, the methodology continues from block 104.

In block 104, the methodology updates the fuel composition value based on the output from the exhaust gas oxygen sensor feedback system. From block 104, the methodology continues to block 106. In block 106, the methodology reenables the flexible fueled vehicle's fuel vapor management system. From block 106, the methodology continues to block 108.

In block 108, the methodology compares the fuel composition sensor's output value to the fuel composition value learned from by the exhaust gas oxygen sensor feedback system. From block 108, the methodology continues to decision block 110. In decision block 110, the methodology determines whether the difference between the fuel composition sensor output value and the learned fuel composition from the exhaust gas oxygen sensor feedback system is greater than a rationality threshold value. This rationality threshold value preferably equals a value which corresponds to a 10% fuel-to-air ratio error.

If the difference between the two values is greater than the rationality threshold at decision block 110, the rationality of the fuel composition sensor is deemed to be malfunctioning and the methodology advances to block 112. In block 112, the methodology sets a fault code indicating that the fuel composition sensor rationality is malfunctioning. From block 112, the methodology continues to bubble 114. In bubble 114, the methodology implements a limp-in routine for operating the engine control system without reliance on the fuel composition sensor.

Referring again to decision block 110, if the methodology determines that the difference between the fuel composition sensor output value and the learned fuel composition from the exhaust gas oxygen sensor feedback system is not greater than the rationality threshold, the methodology advances to block 116. In block 116, the methodology stores the fuel composition sensor value as the fully updated fuel composition sensor value. From block 116, the methodology continues to block 118. In block 118, the methodology employs the fuel composition sensor output value in the engine control system for controlling the fuel-to-air operating parameters of the engine. From block 118, the methodology continues to bubble 98 where it returns to bubble 10 of FIG. 1.

Figure 4:
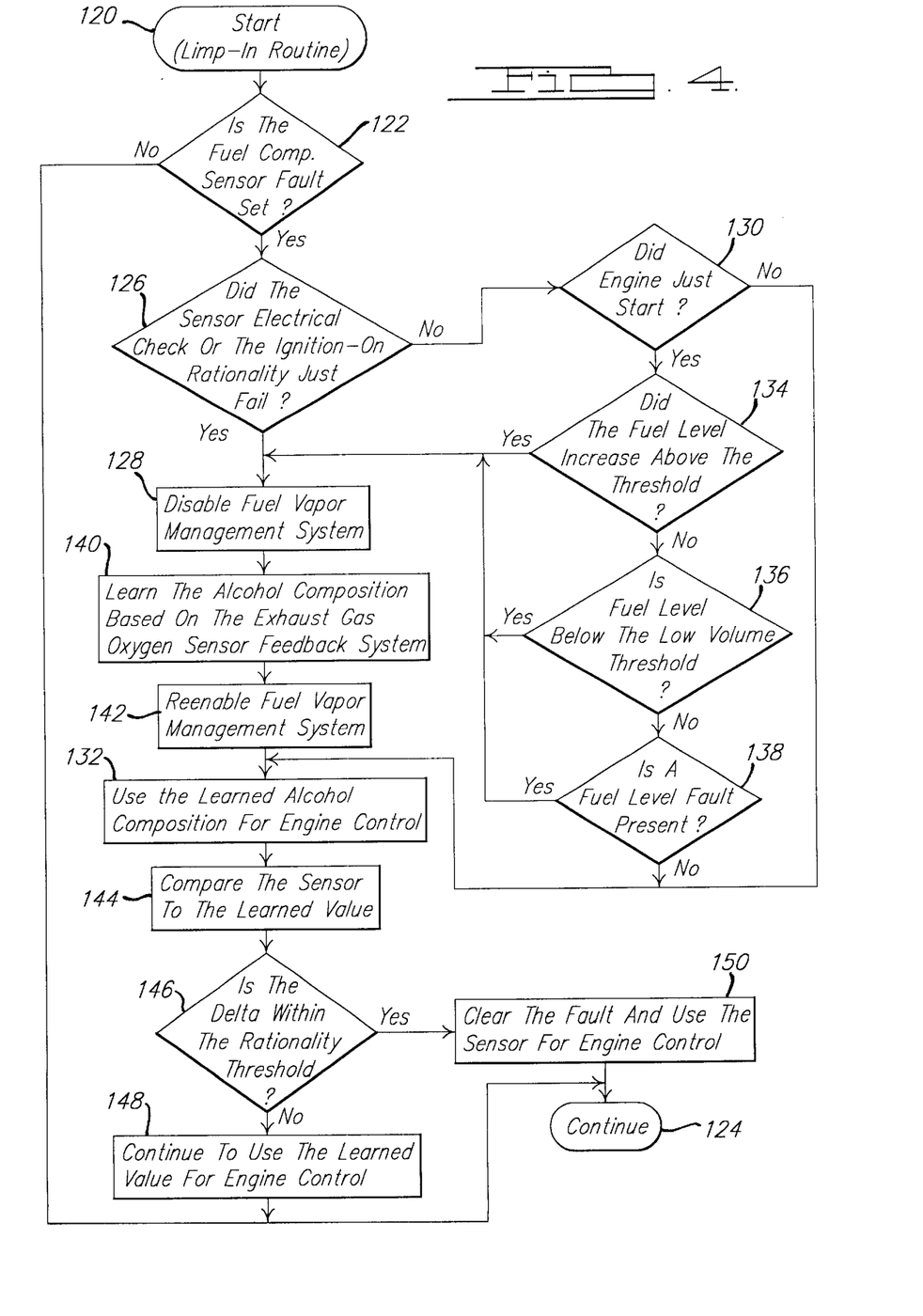
FIG. 4 is a flowchart depicting a methodology for performing a limp-in routine as a result of a malfunctioning fuel composition sensor according to the present invention.

Referring again to bubble 112, after the methodology sets the fuel composition sensor rationality fault code, the methodology advances to bubble 114 and implements a limp-in routine. Turning now to FIG. 4, the limp-in routine is illustrated. The limp-in routine starts in bubble 120 and falls through to decision block 122.

In decision block 122, the methodology determines whether the fuel composition sensor fault code has been set. If not, the methodology advances to bubble 124 and exits the subroutine pending a subsequent execution thereof. However, if the methodology determines that the fuel composition sensor fault code is set at decision block 122, the methodology advances to decision block 126.

In decision block 126, the methodology determines whether the fuel composition sensor electrical check or the ignition-on rationality check just failed. If so, the methodology advances to block 128. However, if the methodology determines that the fuel composition sensor electrical check or the ignition-on rationality check did not just fail at decision block 126, the methodology advances to decision block 130.

In decision block 130, the methodology determines whether the engine has just started. If not, the methodology advances to block 132. However, if the methodology determines that the engine just started at decision block 130, the methodology advances to decision block 134.

In decision block 134, the methodology determines if the fuel level has increased above the fuel volume added threshold. If so, the methodology advances to block 128. However, if the methodology determines that the fuel level has not increased above the fuel added threshold, the methodology advances to decision block 136.

In decision block 136, the methodology determines whether the fuel level is below a low fuel level volume threshold value. If so, the methodology advances to block 128. However, if the methodology determines that the fuel level is not below the low fuel volume threshold value at decision block 136, the methodology advances to decision block 138.

In decision block 138, the methodology determines whether a fuel level sensor fault code is present. If so, the methodology advances to block 128. However, if the methodology determines that no fuel level sensor fault code is present at decision block 138, the methodology advances to block 132.

Referring again to block 128, upon the fuel composition sensor just failing the electrical check or ignition-on rationality check, or upon the fuel level increasing above the added fuel threshold, or the fuel level being below the low-volume threshold, or the presence of a fuel level sensor fault code, the methodology disables the fuel vapor management system.

From block 128, the methodology continues to block 140. In block 140, the methodology learns the composition of the fuel based on the output from the exhaust gas oxygen sensor feedback system. From block 140, the methodology continues to block 142.

In block 142, the methodology reenables the fuel vapor management system. From block 142, the methodology continues to block 132. In block 132, which is also reached from decision block 130, the methodology employs the learned alcohol composition of the fuel from the exhaust gas oxygen sensor feedback system within the engine control system for controlling the fuel-to-air operating parameters of the engine. From block 132, the methodology continues to block 144.

In block 144, the methodology compares the fuel composition sensor output value to the learned fuel composition value from the exhaust gas oxygen sensor feedback system. From block 144, the methodology continues to decision block 146. In decision block 146, the methodology determines whether the difference between the fuel composition sensor output value and the learned fuel composition value from the exhaust gas oxygen sensor feedback system is within the rationality threshold. The rationality threshold preferably equals a value which corresponds to a 10% fuel-to-air ratio error.

If the difference between the two values remains outside of the rationality threshold in decision block 146, the methodology advances to block 148. In block 148, the methodology continues to use the learned fuel composition value from the exhaust gas oxygen sensor feedback system for fuel-to-air engine control. From block 148, the methodology advances to bubble 124 and exits the routine pending a subsequent execution thereof.

However, if the difference between the fuel composition sensor output value and the learned fuel composition value from the exhaust gas oxygen sensor feedback system is within the rationality threshold at decision block 146, the methodology advances to block 150. In block 150, the methodology clears the limp-home mode and uses the fuel composition sensor output value for fuel-to-air engine control while beginning to unmature the fault code. From block 150, the methodology continues to bubble 124 and exits the subroutine pending a subsequent execution thereof.

It should be noted that if any upstream exhaust gas oxygen sensor of the exhaust gas oxygen sensor feedback system is deemed to be malfunctioning when a fuel composition sensor fault occurs, then a calibratible default alcohol fuel composition value is used for fuel-to-air engine control. Further, if any upstream exhaust gas oxygen sensor fault is present without a fuel composition sensor fault, any portion of the fuel composition sensor rationality test that requires exhaust gas oxygen sensor feedback is disabled.

Thus, a methodology for testing the integrity of a fuel composition sensor in a flexible fueled vehicle is provided. At an ignition-on event, the fuel composition sensor is tested for electrical and rational viability. Thereafter, the fuel composition sensor is periodically tested for potential errors. If a potential error is deemed to be occurring, the methodology performs an intrusive test to compare the output from the fuel composition sensor to the output from an exhaust gas oxygen sensor feedback system. If the fuel composition sensor continues to be deemed malfunctioning, engine control is provided by the exhaust gas oxygen sensor feedback system.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, specification, and following claims.

What is claimed is:

1. A method of testing a fuel composition sensor for malfunctions comprising:
   conducting an electrical check of said fuel composition sensor at an ignition-on event;
   conducting a first rationality check of said fuel composition sensor at said ignition-on event;
   conducting a second rationality check of said fuel composition sensor periodically after said ignition-on event; and
   conducting a third rationality check of said fuel composition sensor if said fuel composition sensor fails said second rationality check.

2. The method of claim 1 wherein said electrical check further comprises:
   testing said fuel composition sensor for a shorted high condition;
   testing said fuel composition sensor for a shorted low condition; and
   testing said fuel composition sensor for electrical continuity.

3. The method of claim 1 wherein said first rationality check further comprises:
   determining whether an output voltage from said fuel composition sensor at said ignition-on event is greater than a calibratible amount than a fully updated output voltage from said fuel composition sensor stored prior to said ignition-on event.

4. The method of claim 3 wherein said fully updated output voltage is stored at a last ignition-off event.

5. The method of claim 1 wherein said second rationality check further comprises:

a fuel tank fuel level check;

an injected fuel change check; and a sensor output deviation check.

6. The method of claim 5 wherein said fuel tank fuel level check further comprises:

determining that fuel has been added to a fuel tank;

determining a first fuel composition value assuming that a fuel containing a high concentrate of alcohol was added to the fuel tank;

determining a second fuel composition value assuming that a fuel containing a low concentrate of alcohol was added to the fuel tank; and determining whether an output voltage from said fuel composition sensor is more than a calibratible threshold from either said first fuel composition value and said second fuel composition value.

7. The method of claim 6 wherein said first and second fuel composition values are determined based on a pre-fuel-added fuel composition value, a pre-fuel-added fuel volume, a post-fuel-added fuel volume, and two likely fuel concentrations added.

8. The method of claim 7 wherein said two likely fuel concentrations further comprise:

85% alcohol; and

10% alcohol.

9. The method of claim 5 wherein said injected fuel change check further comprises:

determining whether an amount of fuel delivered to an engine changes by more than a calibratible amount from nominal operating conditions.

10. The method of claim 9 wherein said step of determining whether an amount of fuel delivered to an engine changes by more than a calibratible amount from nominal operating conditions further comprises:

determining whether long-term fuel adaptive values update outside of a given range.

11. The method of claim 5 wherein said sensor output deviation check further comprises:

determining whether a current output voltage from said fuel composition sensor deviates by more than a calibratible amount from a stored fully updated output voltage from said fuel composition sensor.

12. The method of claim 1 wherein said third rationality check further comprises:

determining whether a fuel composition detected by said fuel composition sensor is greater than a calibratible amount than a second fuel composition determined by an engine exhaust gas oxygen sensor feedback system.

13. In combination with the method of testing the fuel composition sensor of claim 1, an engine control method comprising:

converting a basis for a fuel-to-air setting from an output signal from said fuel composition sensor to feedback from an engine exhaust gas oxygen sensor system if said fuel composition sensor fails any one of said electrical check, first rationality check, and third rationality check.

* * * * *